(12) United States Patent
Goldman et al.

(10) Patent No.: US 9,302,954 B2
(45) Date of Patent: Apr. 5, 2016

(54) AROMATIZATION OR DEHYDROCYCLIZATION OF N-ALKANES USING SOLUBLE TRANSITION METAL COMPLEXES

(71) Applicants: Alan Goldman, New Brunswick, NJ (US); Ritu Ahuja, New Brunswick, NJ (US); William Schinski, New Brunswick, NJ (US)

(72) Inventors: Alan Goldman, New Brunswick, NJ (US); Ritu Ahuja, New Brunswick, NJ (US); William Schinski, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/657,723

(22) Filed: Oct. 22, 2012

(65) Prior Publication Data

US 2013/0123552 A1 May 16, 2013

Related U.S. Application Data

(60) Provisional application No. 61/549,570, filed on Oct. 20, 2011.

(51) Int. Cl.
*C07C 5/52* (2006.01)
*C07C 5/50* (2006.01)
*C07C 5/31* (2006.01)

(52) U.S. Cl.
CPC ... *C07C 5/52* (2013.01); *C07C 5/31* (2013.01); *C07C 2531/24* (2013.01)

(58) Field of Classification Search
USPC ........................................ 585/414, 418, 419
See application file for complete search history.

(56) References Cited

PUBLICATIONS

Ahuja et al., Dec. 2010, Catalytic dehydrogenation of n-alkanes by pincer-ligated iridium complexes, Nature-Chemistry, vol. 3, pp. 167-171.*
Haenel et al., 2001, Thermally stable homogeneous catalysts for alkane dehydrogenation, Angew. Chem. Int. Ed., vol. 40, No. 19, pp. 3596-3600.*
Goldman et al., 2004, Alkane transfer-dehydrogenation catalyzed by a pincer-ligated iridium complex, ACS Symposium Series 885, Activation and Functionalization of C-H Bonds, pp. 198-215.*
Rosi et al., 2003, Hydrogen storage in microporous metal-organic frameworks, Science, vol. 300, pp. 1127-1129.*
Kagan et al., 1992, Catalytic asymmetric Diels-Alder reactions, Chemical Reviews, vol. 92, pp. 1007-1019.*
Zhu et al., Highly effective pincer-ligated iridium catalysts for alkane dehydrogenation. DFT calculations of relevant thermodynamics, kinetic, and spectroscopic properties, 2004, J.Am. Chem. Soc. vol. 126, pp. 13044-13053.*
Churchill et al., Comparative studies of dehydrocyclization of n-octane and iso-octane on bifunctional and monofunctional Pt/Al2O3 catalysts, 1993, Chem. Eng. Technol., vol. 16, pp. 10-16.*
Ahuja et al., "Catalytic dehydroaromatizaiton of *n*-alkanes by pincer-ligated iridium complexes", *Nature Chemistry*, vol. 3, 167-171 (2011).
Dittmeyer et al., "Membrane reactors for hydrogenation and dehydrogenation processes based on supported palladium", *J. Mol. Catal. A: Chem.*, 173, 135-184 (2001).
Huang et al., "Ligand exchanges and selective catalytic hydrogenation in molecular single crystals", *Nature* 465, 598-601 (2010).
Kagan et al., "Catalytic Asymmetric Diels- Alder Reaction," *Chemical Reviews*, 92, 1007-1019 (1992).

(Continued)

*Primary Examiner* — In Suk Bullock
*Assistant Examiner* — Youngsul Jeong
(74) *Attorney, Agent, or Firm* — Viksnins Harris & Padys PLLP

(57) ABSTRACT

The invention provides methods and compositions useful for synthesizing alkylaromatics from an n-alkanes.

21 Claims, 1 Drawing Sheet

(56) References Cited

PUBLICATIONS

Okuhara, "Water-Tolerant Solid Acid Catalysts", *Chemical Reviews 102*, 3641-3666 (2002).

Rosi et al., "Hydrogen storage in microporous metal-organic frameworks", *Science 300*, 1127-1129 (2003).

Sakamoto, et al., "Thermodynamic Properties for Solution of Hydrogen in Palladium-Based Binary Alloys," *Ber. Bunsenges. Phys. Chem. 99* (6), 807-820 (1995).

Van Koten et al., "Periphery-functionalized organometallic dendrimers for homogeneous catalysis", *J Mol Catal A: Chem*, 146, 317-323 (1999).

\* cited by examiner

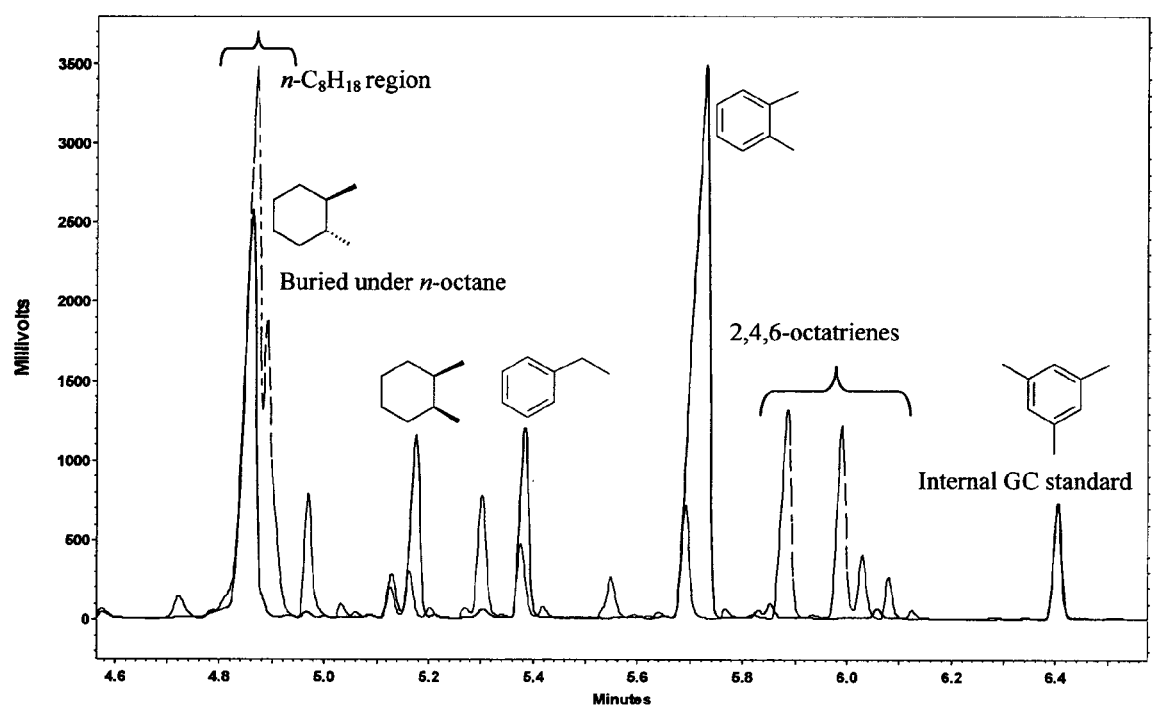

US 9,302,954 B2

AROMATIZATION OR DEHYDROCYCLIZATION OF N-ALKANES USING SOLUBLE TRANSITION METAL COMPLEXES

PRIORITY OF INVENTION

This application claims priority to U.S. Provisional Application No. 61/549,570 that was filed on Oct. 20, 2011. The entire content of this provisional application is hereby incorporated by reference herein.

STATEMENT OF GOVERNMENT SUPPORT

This invention was made with government support under Grant #DE-FG02-93ER14353 awarded by the Department of Energy and Grant #CHE-0650456 awarded by the National Science Foundation. The government has certain rights in the invention.

BACKGROUND

Alkyl aromatics are currently synthesized commercially on an enormous scale (about. 40 million tons per annum), typically by the alkylation of arenes using the corresponding arenes and olefins. Improved methods of synthesis of alkyl aromatic compounds are needed.

SUMMARY OF CERTAIN EMBODIMENTS OF THE INVENTION

Certain embodiments of the present invention provide methods of synthesizing an alkylaromatic from an n-alkane comprising the step of contacting the n-alkane with a soluble transition metal catalyst.

In certain embodiments, the step of contacting the n-alkane with a soluble transition metal catalyst is performed at a temperature of from about 150° C. to about 175° C.

In certain embodiments, the step of contacting the n-alkane with a soluble transition metal catalyst is performed at a temperature of about 165° C.

In certain embodiments, the step of contacting the n-alkane with a soluble transition metal catalyst is performed at a temperature above 175° C.

In certain embodiments, the soluble transition metal catalyst is a pincer-ligated iridium catalyst.

In certain embodiments, the pincer-ligated iridium catalyst is $(^{iPr}PCP)IrH_4$.

In certain embodiments, the step of contacting the n-alkane with the soluble transition metal catalyst is performed in the presence of an H-acceptor.

In certain embodiments, the H-acceptor is t-butylethylene (TBE), propylene or ethylene.

In certain embodiments, the step of contacting the n-alkane with the soluble transition metal catalyst comprises refluxing or a physical method (e.g., bubbling inert gas through the system) to lose hydrogen.

In certain embodiments, the step of contacting the n-alkane with the soluble transition metal catalyst comprises the use of a hydrogen sponge or a hydrogen-permeable membrane.

In certain embodiments, the hydrogen sponge comprises a metal-organic-framework, a palladium metal or metal alloy, or a crystalline pincer complex.

In certain embodiments, the n-alkane is a $C_6$-$C_{30}$ n-alkane.
In certain embodiments, the n-alkane is a $C_6$-$C_{20}$ n-alkane.
In certain embodiments, the n-alkane is a $C_6$-$C_{12}$ n-alkane.

In certain embodiments, the n-alkane is n-hexane ($C_6$), n-octane ($C_8$), n-decane ($C_{10}$) or n-dodecane ($C_{12}$).

In certain embodiments, the step of contacting the n-alkane with a soluble transition metal catalyst comprises the use of a cyclization co-catalyst.

In certain embodiments, the cyclization co-catalyst is a Lewis acid catalyst.

In certain embodiments, the methods may further comprise identifying the product(s) of the synthesis.

In certain embodiments, the methods may further comprise separating the product(s) of the synthesis.

Certain embodiments of the present invention provide compositions that comprise an n-alkane and a soluble transition metal catalyst.

In certain embodiments, the composition further comprises an H-acceptor.

In certain embodiments, the composition further comprises a cyclization co-catalyst.

In certain embodiments the n-alkane is a $C_6$-$C_{30}$ n-alkene.
In certain embodiments, the n-alkane is a $C_6$-$C_{20}$ n-alkene.
In certain embodiments, the n-alkane is a $C_6$-$C_{12}$ n-alkene.

BRIEF DESCRIPTION OF THE FIGURES

FIG. 1. GC traces of the reaction of n-octane with TBE as a H-acceptor at 165° C. for (a) 4 h (dash) (b) 124 h (solid).

DETAILED DESCRIPTION

Alkyl aromatics are currently synthesized commercially on an enormous scale, typically by the alkylation of arenes using the corresponding arenes and olefins. These feedstocks are generally much more expensive than n-alkanes. Furthermore, as Fischer-Tropsch plants are increasingly put into operation, the price of n-alkanes will likely decline further relative to other hydrocarbon feeds and the price of arenes may increase relative to other hydrocarbon feeds. Accordingly, certain embodiments of the present invention provide methods of synthesis of alkyl aromatics from n-alkanes.

The term n-alkane includes straight hydrocarbons. For example, n-alkanes include $C_6$-$C_{30}$ n-alkanes, $C_6$-$C_{20}$ n-alkanes and $C_6$-$C_{12}$ n-alkanes.

The term n-alkene includes straight hydrocarbons with one or more double bonds.

The term alkyl includes straight or branched hydrocarbons unless otherwise noted. Alkyls, for example, include ($C_1$-$C_8$) alkyls and ($C_1$-$C_6$)alkyls.

The term alkylaromatic includes aromatics such as aryls (e.g. phenyl) that are substituted with one or more alkyl groups.

"Acceptorless" systems (systems without a hydrogen acceptor in which hydrogen is released) may be used in the method described herein. Such systems may involve refluxing or a physical method (e.g., bubbling inert gas through the system) to lose hydrogen. Hydrogen sponges (materials or molecules that absorb hydrogen reversibly) or hydrogen-permeable membranes (e.g., palladium) may also be used. Possible hydrogen sponges include MOF's (metal-organicframeworks), Rosi et al., Science 300, 1127-1129 (2003)), palladium metal or metal alloys, (Sakamoto et al., Ber. Bunsen-Ges. Phys. Chem. Chem. Phys. 99, 807-820 (1995)), crystalline pincer complexes. (Huang et al., Nature 465, 598-601 (2010). These or other such materials could be in contact with the alkane substrates and then recycled after absorbing hydrogen. Hydrogen-permeable membranes are known in the art. (Paglieri et al., Purif. Methods 31, 1-169 (2002); Dittmeyer et al., J. Mol. Catal. A-Chem. 173, 135-184 (2001)).

Co-catalysts may also be used in the methods. In particular, catalysts for cyclization may be used. It is believed at this point that the reaction proceeds via dehydrogenation sequentially through monoenes, dienes and trienes. The trienes then undergo cyclization (to give cyclohexadienes) and then further dehydrogenation to give aromatics. It is unclear at this point if the iridium catalyst only affects dehydrogenation. The trienes may cyclize spontaneously or, alternatively, the iridium catalyst may promote cyclization. In either case, addition of a cyclization co-catalyst may greatly promote the overall reaction rates and/or yields. For example, Lewis acid catalysts may be used to catalyze electrocyclization reactions. (Kagan et al., Chemical Reviews 92, 1007-1019 (1992); Okuhara, Chemical Reviews 102, 3641-3665 (2002)).

Dehydrogenation catalysts other than $(^{iPr}PCP)IrH_4$ may also be used, including other derivatives of the $(^{iPr}PCP)Ir$ group, other pincer-ligated iridium complexes (both "PCP" type and otherwise), and other soluble catalysts. There are many pincer catalysts and other potential catalysts. (van Koten et al., J. Mol. Catal. A: Chem. 146, 317-323 (1999); The Chemistry of Pincer Compounds; Morales-Morales, D.; Jensen, C., Eds.; Elsevier: Amsterdam, 2007).

In one embodiment the soluble transition metal catalyst is $(^RPCP)Ir$:

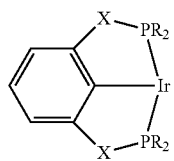

wherein each R is independently alkyl, and each X is independently $CH_2$ or O.

In another embodiment the soluble transition metal catalyst is $(^RPCP)Ir$:

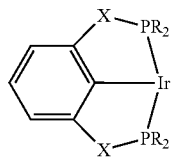

wherein R is i-Pr or other alkyl, and each X is independently $CH_2$ or O.

In another embodiment the soluble transition metal catalyst is:

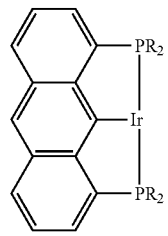

wherein each R is independently alkyl.
A specific value for alkyl is $(C_1-C_6)$alkyl.
A specific value for X is O.
Another specific value for X is $CH_2$.
A specific value for R is i-Pr (e.g. isopropyl).
Certain embodiments of the invention will now be illustrated by the following non-limiting Example.

EXAMPLE 1

Aromatization or Dehydrocyclization of n-alkanes Using Soluble Transition Metal Complexes Alkylaromatics are commercially produced on a scale of ca. 60 billion pounds/year using arene-olefin coupling strategies. The direct conversion of n-alkanes to alkylaromatics (via alkane aromatization or dehydrocyclization) is currently not a commercially viable process. However, n-alkanes present a potential feedstock that is economically quite attractive relative to arenes and olefin, and will probably become more so due to the increasing use of Fischer-Tropsch technology which yields n-alkanes from methane or other sources of syngas.

There are several literature reports of aromatization of aliphatic hydrocarbons (n-alkanes) using heterogeneous catalyst systems operating at high temperatures (ca. 500° C.). These reactions yield a mixture of various aromatic compounds. In particular, substantial quantities of compounds with carbon-number lower than the alkane feedstock are produced, as a result of "cracking" or "clipping" of the initial alkylaromatic products, which occurs at elevated temperatures over typical aromatization catalysts.

In the present invention, milder routes to aromatization or dehydrocyclization of n-alkanes using soluble transition metal catalysts are described. Accordingly, it will be possible to employ inexpensive and abundant n-alkanes as feedstock for alkylaromatic production.

The present invention includes examples where the system shows high selectivity, with minimal or no cracking. Thus, advantages of the invention include milder conditions (reactions carried out at moderate temperature) and high selectivity. For example, using propylene as a hydrogen-acceptor, the reaction of n-octane at 165° C. yields ca. 46% o-xylene with only 7% ethylbenzene. Only 1% benzene and ca. 0.1% toluene were formed with no observable formation of m-xylene, or p-xylene.

Results and Discussion

The present invention describes aromatization of n-alkanes to form arenes, primarily ortho-substituted, using a "pincer"-ligated iridium catalyst. $(^{iPr}PCP)IrH_4$ $(^{iPr}PCP=\kappa^3-C_6H_3-2,6-[CH_2P(i-C_3H_7)_2]_2)$, as an alkane dehydrogenation catalyst.

The reactions have been carried in the presence of an excess of a H-acceptor (e.g. t-butylethylene (TBE) or propylene) (Scheme 1).

Scheme 1: Aromatization or Dehydrocyclization of n-alkanes using pincer-ligated ($^{i\text{-}Pr}$PCP)IrH$_4$.

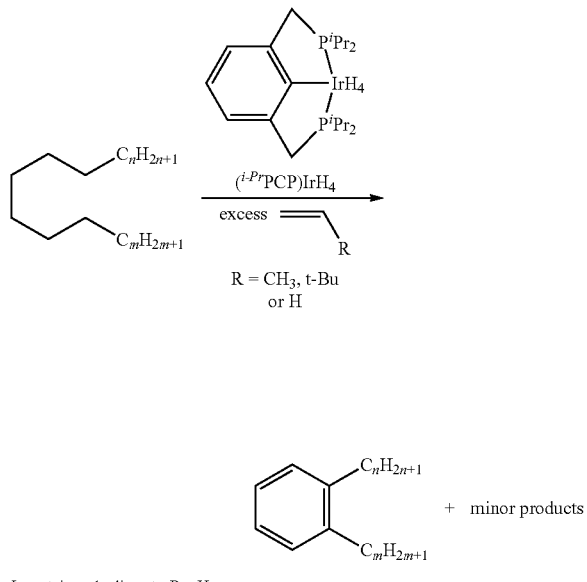

In certain embodiments, R = H.

Four different exemplary n-alkanes, namely n-hexane (C$_6$), n-octane (C$_8$), n-decane (C$_{10}$) and n-dodecane (C$_{12}$) have been employed in the present invention in the presence of 2-4 equivalents of H-acceptor with respect to the n-alkane at 165° C. to provide examples of the concept.

Scheme 1a: Aromatization or Dehydrocyclization of n-alkanes.

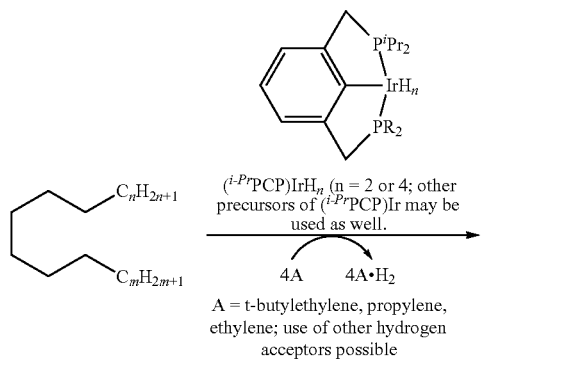

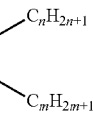

Scheme 1b: Aromatization or Dehydrocyclization of n-alkanes.

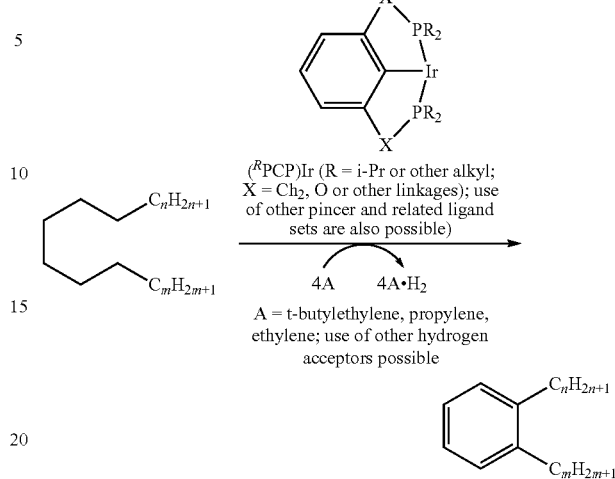

In certain embodiments n+m=0-24. In certain embodiments n+m=0-14. In certain embodiments n+m=0-4.

(I) Reaction with n-hexane

Reactions of n-hexane were carried out at 165° C. Solutions were prepared in mesitylene (this was originally done to facilitate operating at higher temperatures since the b.p. of mesitylene is 165° C.). The reaction was carried out using 5 mM ($^{iPr}$PCP)IrH$_4$ catalyst in the presence of 3.21 M TBE (3 equivalents with respect to n-hexane) and 3.2 M mesitylene at 165° C. The reaction was followed by GC at regular time intervals. The results obtained are given in Table 1.93% of n-hexane was consumed in the reaction giving 47% benzene formation with respect to the starting concentration of n-hexane (obtained from GC of the solution before heating). In addition to C$_6$ products, 55 mM C$_6$-C$_6$ coupling products was also obtained.

TABLE 1

Aromatization of n-hexane with TBE as H-acceptor (concentrations from GC). ($^{iPr}$PCP)IrH$_4$ (5 mM) n-hexane (1.07M), TBE (3.21M), mesitylene (3.2M) at 165° C.

| Time (h) | [C$_6$H$_6$] (mM) | cis-HD$^a$ (mM) | trans-HD$^a$ (mM) | [C$_6$]$^b$ (mM) | n-hexane consumed (%) |
|---|---|---|---|---|---|
| 1 | 0 | 99 | 138 | 243 | 58 |
| 3 | 41 | 146 | 193 | 232 | 71 |
| 6 | 72 | 165 | 217 | 204 | 76 |
| 23 | 159 | 144 | 192 | 147 | 86 |
| 48 | 242 | 114 | 164 | 117 | 90 |
| 118 | 430 | 73 | —$^c$ | 88 | 93 |
| 192 (8 d) | 444 | 49 | —$^c$ | 83 | 93 |

$^a$cis-HD = cis, trans-2,4-hexadiene; trans-HD = trans, trans-2,4-hexadiene.
$^b$Sum of other unidentified C$_6$ acyclic and cyclic olefins.
$^c$Well overlapped with benzene in GC.

(II) Reaction with Higher n-alkanes (n≥8)

Reactions with higher n-alkanes such as n-decane and n-dodecane were initially conducted using mesitylene as solvent. However, reactions with neat n-alkane solution gave results not significantly different from those done in the presence of mesitylene and thus later reactions (using TBE as H-acceptor) were carried out without mesitylene. The reactions were conducted with 5 mM ($^{iPr}$PCP)IrH$_4$ catalyst, and either 3 or 4 equiv H-acceptor (TBE), at 165° C., in sealed glass tubes. All reactions were followed by GC at regular time intervals.

(i) Reaction of n-octane with TBE as H-acceptor

Table 2 and FIG. 1 give data obtained from the reaction of n-octane with TBE as the H-acceptor. GC of the reaction (FIG. 1) at early reaction times showed the formation of certain intermediates (Retention time=5.88-6.1 min in GC) which diminished after prolonged heating. These intermediates were identified as mixture of various isomers of 2,4,6-octatrienes by GC-MS (M=108) and by independent synthesis following a literature procedure. (Jacobson et al., J. Org. Chem. 1985, 50, 194) When the reaction reached completion (after 5 days of heating), GC-MS was used to identify the products detected by GC. About 85% of n-octane was consumed in the reaction after 2 days of heating. After 5 days, o-xylene (634 mM) was obtained as the major compound along with ethylbenzene in smaller quantities (121 mM). No m-xylene or p-xylene were observed. In addition to these aromatic products, $C_8$-olefins, cis-dimethylcyclohexane (124 mM), and trans-dimethylcyclohexane (65 mM) were also formed. No significant cracking (only 1% benzene) was observed in these reactions. In addition to $C_8$ products, 93 mM of $C_8$-$C_8$ coupling products was also obtained. A total of 46% of aromatic products were produced in the reaction.

TABLE 2

Aromatization of n-octane using TBE as H-acceptor (concentrations obtained from GC). 5 mM ($^{iPr}$PCP)IrH$_4$, 1.81M n-octane, 5.44M TBE at 165° C. Selectivity for o-xylene = ratio of o-xylene to all other aromatic products.

| Time (h) | [o-xylene] (mM) | [Ethyl benzene] (mM) | Selectivity for o-xylene (%) | Cis-dimethyl-cyclohexane (mM) | Trans-dimethyl-cyclohexane (mM)[a] | n-octane consumed (%)[a] |
|---|---|---|---|---|---|---|
| 1 | 3 | 19 | 14 | 3 | 1.6 | 38 |
| 2 | 13 | 24 | 31 | 6 | 3 | 48 |
| 4 | 68 | 46 | 57 | 27 | 14 | 68 |
| 7 | 168 | 73 | 68 | 63 | 33 | 79 |
| 23 | 386 | 109 | 77 | 169 | 89 | 83 |
| 47 | 507 | 112 | 81 | 131 | 69 | 85 |
| 124 | 640 | 125 | 83 | 124 | 65 | 82 |

[a]Trans-dimethylcyclohexane overlaps with n-octane in GC (on a 25-m column). To estimate its concentration, the GC was run for one sample (after 124 h) on a 100-m column to separate the two compounds. The concentration of trans-dimethylcyclohexane was found to be 61 mM, giving the ratio of cis-(116 mM) to trans-dimethylcyclohexane as 1.9:1. Assuming a similar ratio throughout the reaction, the percent of n-octane consumed during the reaction was calculated by subtracting the conc. of trans-dimethylcyclohexane.

(ii) Reaction of n-octane with Propylene as H-acceptor

Table 3 gives the data for the reaction of n-octane in the presence of propylene as H-acceptor at 165° C. After heating for 4 days, 54% aromatics were obtained with 85% selectivity for o-xylene. A negligible amount of cracking was observed giving just 1.2% of benzene. Overall >99% of n-octane was consumed in the reaction.

TABLE 3

Aromatization of n-octane using propylene as H-acceptor (concentrations obtained from GC). 5 mM ($^{iPr}$PCP)IrH$_4$, 0.61M n-octane, 6.47M mesitylene, approx. 60 mL propylene gas (800 torr) at 165° C. Selectivity for o-xylene = ratio of o-xylene to all other aromatic products

| Time (h) | [o-xylene] (mM) | [Ethyl benzene] (mM) | Selectivity for o-xylene (%) | Cis-dimethyl cyclo-hexane (mM) | Trans-dimethyl cyclo-hexane (mM) | n-octane consumed (%) |
|---|---|---|---|---|---|---|
| 24 | 192 | 44 | 80 | 22 | 12 | 97 |
| 96 | 277 | 44 | 85 | 12 | 6 | >99 |

(ii) Reaction of n-octane with Ethylene as H-acceptor

Table 4 gives the data for the reaction of n-octane in the presence of ethylene as H-acceptor at 165° C. Ethylene also served as a good H-acceptor although the reaction was slower as compared to the reaction carried out with propylene. Overall conversion obtained in this reaction was lower (44% aromatics) than what was obtained in the reaction with propylene.

TABLE 4

Aromatization of n-octane using ethylene as H-acceptor (concentrations obtained from GC). 5 mM ($^{iPr}$PCP)IrH$_4$, 0.61M n-octane, 6.47M mesitylene, approx. 60 mL ethylene gas (800 torr) at 165° C. Selectivity for o-xylene = ratio of o-xylene to all other aromatic products.

| Time (h) | [o-xylene] (mM) | [Ethyl benzene] (mM) | Selectivity for o-xylene (%) | Cis-dimethyl cyclo-hexane (mM) | Trans-dimethyl cyclo-hexane (mM) | n-octane consumed (%) |
|---|---|---|---|---|---|---|
| 24 | 44 | 21 | 66 | 9 | 5 | 69 |
| 96 | 173 | 32 | 83 | 5 | 3 | 88 |
| 168 | 213 | 30 | 86 | 4 | 2 | 91 | b) Reaction with n-decane

Under conditions similar to those used in reaction of n-octane with 3 eq. of TBE, the reaction of n-decane with 4 eq. of TBE, yielded o-propyltoluene as the major aromatic product (Table 5). A small amount of benzene (56 mM) due to cracking was also obtained. After 5 days of heating at 165° C., 443 mM o-propyltoluene was obtained with around 29 mM 1,2-diethylbenzene and 32 mM n-butyl benzene totaling to 37% of aromatic products. After the completion of the reaction, $C_{10}$-$C_{10}$ coupling products (63 mM) were also obtained in the reaction consuming 93% of n-decane.

TABLE 5

Aromatization of n-decane using TBE as H-acceptor (concentrations obtained from GC). 5 mM ($^{iPr}$PCP)IrH$_4$, 1.41M n-decane, 5.63M TBE at 165° C. Selectivity for o-propyltoluene = ratio of o-propyltoluene to all other aromatic products.

| Time (h) | [o-propyl toluene] (mM) | [n-butyl benzene] (mM) | [Diethyl benzene] (mM) | Selectivity for o-propyl toluene (%) | [$C_6H_6$] (mM) | n-decane consumed (%) |
|---|---|---|---|---|---|---|
| 1 | 0 | —[a] | — | — | 10 | 45 |
| 3 | 17 | —[a] | —[a] | — | 28 | 59 |

TABLE 5-continued

Aromatization of n-decane using TBE as H-acceptor (concentrations obtained from GC). 5 mM ($^{iPr}$PCP)IrH$_4$, 1.41M n-decane, 5.63M TBE at 165° C. Selectivity for o-propyltoluene = ratio of o-propyltoluene to all other aromatic products.

| Time (h) | [o-propyl toluene] (mM) | [n-butyl benzene] (mM) | [Diethyl benzene] (mM) | Selectivity for o-propyl toluene (%) | [C$_6$H$_6$] (mM) | n-decane consumed (%) |
|---|---|---|---|---|---|---|
| 5 | 29 | —$^a$ | —$^a$ | — | 43 | 69 |
| 23 | 287 | 20 | 14 | 76 | 56 | 87 |
| 52 | 376 | 26 | 23 | 77 | 60 | 91 |
| 120 | 443 | 32 | 29 | 79 | 56 | 93 |

$^a$Difficult to estimate due to extensive overlap with intermediates formed in the reaction.

c) Reaction with n-dodecane

The reaction with n-dodecane (with 3 eq. of TBE), under conditions similar to those above, yielded o-pentyltoluene as the major aromatic product (Table 6). After 5 days of heating at 165° C., 74% of n-dodecane was consumed giving 211 mM o-pentyltoluene with 13 mM n-hexylbenzene (phenyl hexane). Along with C$_{12}$ compounds, "cracking" was also observed yielding 197 mM n-hexane, 216 mM benzene and 64 mM C$_{12}$-C$_{12}$ coupling products. Thus the reaction yielded a total of 29% of aromatic products. With 4 eq. of TBE, a total of 36% aromatics were obtained with 44% selectivity for o-pentyltoluene, consuming 89% of n-dodecane.

TABLE 6

Aromatization of n-dodecane using TBE as H-acceptor (concentrations obtained from GC). 5 mM ($^{iPr}$PCP)IrH$_4$, 1.63M n-dodecane, 4.86M TBE at 165° C. Selectivity for o-pentyltoluene = ratio of o-pentyltoluene to all other aromatic products.

| Time (h) | [o-pentyl toluene] (mM) | [Phenyl hexane] (mM) | Sum of C$_6$-olefins (mM) | [C$_6$H$_6$] (mM) | [n-C$_6$H$_{14}$] (mM) | Selectivity for o-pentyl toluene (%) | n-dodecane consumed (%) |
|---|---|---|---|---|---|---|---|
| 1 | 3 | — | 77 | 8 | 0 | 27 | 42 |
| 3 | 21 | — | 204 | 18 | 21 | 54 | 54 |
| 5 | 36 | — | 42 | 177 | 74 | 17 | 62 |
| 24 | 174 | 13 | 0 | 222 | 198 | 43 | 74 |
| 47 | 200 | 14 | 0 | 227 | 204 | 45 | 73 |
| 119 | 211 | 13 | 0 | 216 | 197 | 48 | 72 |

Experimental Section
Materials and Methods
General Considerations

All manipulations were carried out using standard Schlenk and glove box techniques. n-hexane (>99%) was purchased from Fluka. n-octane, n-decane, n-dodecane, tert-butylethylene (TBE; 3,3-dimethyl-1-butene), p-xylene and mesitylene were purchased from Aldrich. Research grade propylene and ethylene gas was obtained from Matheson and used as received. All liquids were degassed via several freeze-pump-thaw cycles, stirred and dried over Na-K, collected and then stored under argon in the glove box. ($^{iPr}$PCP)IrH$_4$ was synthesized as reported.[1] GC-MS measurements were performed with a HP 5890 Series II Plus instrument fitted with a Varian CP-Sil 5 CB capillary column (15 m×0.25 mm ID×0.25 μm film thickness). Most of the GC analyses (FID detection) were performed on a Thermo Electron Corporation Focus GC instrument fitted with either an Agilent HP-1 100% methyl silicone gum column: 25 m length×0.2 mm ID×0.5 μm film thickness using GC method A given below. In certain cases, GC analyses were carried out using Petrocol-DH column from Supelco: 100 m length×0.25 mm ID ×0.5 μm film thickness using the following GC method B:

GC Method A
Detector: FID
Starting temperature: 40° C.
Time at starting temp: 1.4 min
Ramp1: 20° C./min up to 250° C. with hold time=3 min
Ramp2: 20° C./min up to 300° C.
Ending temperature: 300° C.
Flow rate: 1 mL/min (He)
Split ratio: 25
Inlet temperature: 300° C.
Detector temperature: 350° C.
GC Method B (Used Only for Identifying trans-dimethylcyclohexane and Some of the Intermediates Formed in the Aromatization Reaction of n-hexane)
Detector: FID
Starting temperature: 60° C.
Time at starting temp: 90 min
Ramp 1: 20° C./min up to 250° C.
Ending temperature: 250° C.
Flow rate: 1 mL/min (He)
Split ratio: 25
Inlet temperature: 230° C.
Detector temperature: 250° C.
With tert-butylethylene (TBE) as H-Acceptor
Representative Procedure for Aromatization of n-hexane In the glovebox, ($^{iPr}$PCP)IrH$_4$ (2.7 mg, 0.005 mmol) was dissolved in mesitylene (0.44 mL, 3.16 mmol), n-hexane (0.14 mL, 1.07 mmol) and TBE (0.42 mL, 3.21 mmol; n-hexane: TBE=1:3) was added to the solution containing p-xylene (10 μl, 81.1 mM as an internal standard). Aliquots of this solution (0.1 mL each) were transferred to multiple 5-mm glass tubes. The contents were cooled under liquid nitrogen and then sealed under vacuum. These sealed tubes were heated (in parallel) in a preheated oven at 165° C. At regular intervals, a tube was brought to room temperature and the sample was analyzed by GC.

Representative Procedure for Aromatization of n-octane, n-decane and n-dodecane

A similar procedure as mentioned for reactions with n-hexane was adopted for reactions with n-octane, n-decane and n-dodecane except that these reactions were carried out in neat n-alkanes without mesitylene. The n-alkane to TBE ratio was maintained either as 1:3 or 1:4. The reaction was followed by GC and the major products were also confirmed with GC-MS. The reactions were tried both in presence and absence of mesitylene.
With Propylene or Ethylene as H-acceptor
Representative Procedure for Aromatization of n-octane In the glovebox, ($^{iPr}$PCP)IrH$_4$ (2.7 mg, 0.005 mmol) was dissolved in mesitylene (0.9 mL, 6.47 mmol) and n-octane (0.1 mL, 0.61 mmol) was added. This solution (1.0 mL) was then transferred to a Schlenk flask (approx. 60 mL total volume) containing a micro stir bar fitted with a Kontes valve and an o-ring joint. The contents were cooled under liquid nitrogen and the solution was degassed via freeze-pump-thaw cycles. Then the solution was brought to room temperature and then propylene or ethylene (800 torr) was passed into the flask at room temperature. The flask was immersed and the solution stirred in a preheated oil bath maintained at 165° C. After 24 h of heating, the flask was removed from the oil bath and brought to room temperature. The solution was then cooled in liquid nitrogen and the flask was evacuated to remove excess of gas and the flask transferred to the glove box. The reaction mixture was then analyzed by GC. Again fresh propylene or ethylene was charged into the flask in a similar manner as mentioned above. The contents were heated again and the reaction was continued in a similar fashion until there was no change in the concentration of the products (as seen in GC).

Certain aspects of the present invention are described in Ahuja et at, *Nat. Chem.*, 3, 167 (2011), which publication is incorporated herein by reference.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. A method of synthesizing an alkylaromatic hydrocarbon from an n-alkane comprising the step of contacting the n-alkane with a pincer-ligated iridium catalyst wherein the pincer-ligated iridium catalyst is selected from:

(a) ($^R$PCP)Ir:

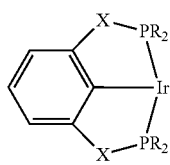

wherein each R is independently alkyl, and each X is independently $CH_2$ or O;

(b) ($^R$PCP)Ir:

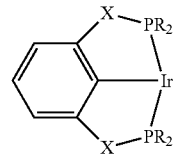

wherein R is i-Pr or other alkyl, and each X is independently $CH_2$ or O;

(c) ($^{iPr}$PCP)IrH$_n$, wherein n is 2 or 4;
   (d) ($^{iPr}$PCP)IrH$_4$; and
   (e)

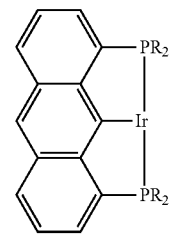

wherein each R is independently alkyl.

2. The method of claim 1, wherein the step of contacting the n-alkane with the pincer-ligated iridium catalyst is performed at a temperature above 175° C.

3. The method of claim 1, wherein the step of contacting the n-alkane with the pincer-ligated iridium catalyst is performed at a temperature of from about 150° C. to about 175° C.

4. The method of claim 1, wherein the step of contacting the n-alkane with the pincer-ligated iridium catalyst is performed at a temperature of about 165° C.

5. The method of claim 1, wherein the pincer-ligated iridium catalyst is ($^R$PCP)Ir:

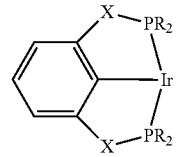

wherein each R is independently alkyl, and each X is independently $CH_2$ or O.

6. The method of claim 1, wherein the pincer-ligated iridium catalyst is ($^R$PCP)Ir:

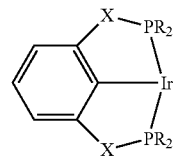

wherein R is i-Pr or other alkyl, and each X is independently $CH_2$ or O.

7. The method of claim 1, wherein the pincer-ligated iridium catalyst is $(^{iPr}PCP)IrH_n$, wherein n is 2 or 4.

8. The method of claim 1, wherein the pincer-ligated iridium catalyst is $(^{iPr}PCP)IrH_4$.

9. The method of claim 1, wherein the step of contacting the n-alkane with the pincer-ligated iridium catalyst is performed in the presence of a H-acceptor.

10. The method of claim 9, wherein the H-acceptor is t-butylethylene (TBE), propylene or ethylene.

11. The method of claim 1 wherein the step of contacting the n-alkane with the pincer-ligated iridium catalyst comprises refluxing or a physical method to remove hydrogen.

12. The method of claim 1, wherein the step of contacting the n-alkane with the pincer-ligated iridium catalyst comprises the use of a hydrogen sponge or a hydrogen-permeable membrane.

13. The method of claim 12, wherein the hydrogen sponge comprises a metal-organic-framework, a palladium metal or metal alloy, or a crystalline pincer complex.

14. The method of claim 1, wherein the n-alkane is a $C_6$-$C_{30}$ n-alkane.

15. The method of claim 1, wherein the n-alkane is n-hexane ($C_6$), n-octane ($C_8$), n-decane ($C_{10}$) or n-dodecane ($C_{12}$).

16. The method of claim 1, wherein the step of contacting the n-alkane with the pincer-ligated iridium catalyst comprises a use of a cyclization co-catalyst.

17. The method of claim 16, wherein the cyclization co-catalyst is a Lewis acid catalyst.

18. The method of claim 1, further comprising identifying a product(s) of the synthesizing the alkylaromatic hydrocarbon.

19. The method of claim 1, further comprising separating a product(s) of the synthesizing the alkylaromatic hydrocarbon.

20. The method of claim 1, wherein the pincer-ligated iridium catalyst is:

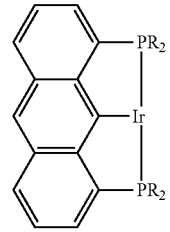

wherein each R is independently alkyl.

21. The method of claim 1 wherein the pincer-ligated iridium catalyst is a soluble pincer-ligated iridium catalyst.

* * * * *